US012629348B2

(12) United States Patent (10) Patent No.: US 12,629,348 B2
Faulkner et al. (45) Date of Patent: May 19, 2026

(54) METHOD AND COMPOSITION FOR TREATING OSTEOARTHRITIS

(71) Applicant: Vireo Systems, Inc., Madison, TN (US)

(72) Inventors: Mark C. Faulkner, Madison, TN (US); Donald W. Miller, Winnipeg (CA); Gary Crawford, Winnipeg (CA)

(73) Assignee: Vireo Systems, Inc., Madison, TN (US)

( * ) Notice: Subject to any disclaimer, the term of this patent is extended or adjusted under 35 U.S.C. 154(b) by 839 days.

(21) Appl. No.: 17/582,595

(22) Filed: Jan. 24, 2022

(65) Prior Publication Data

US 2022/0218644 A1 Jul. 14, 2022

Related U.S. Application Data

(63) Continuation of application No. 14/572,159, filed on Dec. 16, 2014, now abandoned.

(60) Provisional application No. 61/916,312, filed on Dec. 16, 2013.

(51) Int. Cl.
*A61K 31/221* (2006.01)
*A61K 31/22* (2006.01)
*A61K 45/06* (2006.01)

(52) U.S. Cl.
CPC ............ *A61K 31/221* (2013.01); *A61K 31/22* (2013.01); *A61K 45/06* (2013.01)

(58) Field of Classification Search
CPC ....... A61K 31/221; A61K 31/22; A61K 45/06
See application file for complete search history.

(56) References Cited

U.S. PATENT DOCUMENTS

| | | | |
|---|---|---|---|
| 5,885,597 A | 3/1999 | Botknecht | |
| 8,147,882 B2 | 4/2012 | Lomax | |
| 2001/0006671 A1 | 7/2001 | Goodman et al. | |
| 2003/0144219 A1 | 7/2003 | Phinney et al. | |
| 2011/0224174 A1 | 9/2011 | Miller | |

OTHER PUBLICATIONS

Anilkumar 2010 Ethnomedicine: A Source of Complementary Therapeutics, 2010: 267-293. (Year: 2010).*

Choi et al. Antiinflammatory, analgesic and antioxidant activities of the fruit of Foeniculum vulgare, Fitoterapia 75 (2004) 557-565 (Year: 2004).*
Brenner et al. A review of the application of inflammatory biomarkers in epidemiologic cancer research Cancer Epidemiol Biomarkers Prev (2014) 23 (9): 1729-1751. (Year: 2014).*
De Seny et al. (2013) Acute-Phase Serum Amyloid A in Osteoarthritis: Regulatory Mechanism and Proinflammatory Properties. PLoS One 8(6): e66769 (Year: 2103).*
Walpole, Sarah et al., BMC Public Health, 2012, 12:439.
Sandersoln et al., Systematic review of the management of canine osteoarthritis, (2009), Systematic review of the management of canine osteoarthritis Veterinary Record, 164, 418-424. Abstract only (Year: 2009).
Shin, Jang-Woo et al., "Interpretation of Animal Dose and Human Equivalent Dose for Drug Development", The Journal of Korean Oriental Medicine 2010, vol. 31, No. 3, 1-7.
Singh, M.P. et al., Topical Gel: A Homogenous Preparation, International Journal of Pharmaceutical Research and Bio-Science, 2013, vol. 2(5): 424-437, ISSN: 2277-8713, Accepted Date Jul. 28, 2013; Published Date: Oct. 27, 2013.
Poolsup, Nalinee et al., Glucosamine Long-Term Treatment and the Progression of Knee Osteoarthritis: Systematic Review of Randomized Controlled Trials, The Annals of Pharmacotherapy Jun. 2005, vol. 39, pp. 1080-1087.
Altman et al., Development of Criteria for the Classification and Reporting of Osteoarthritis, Arthritis and Rheumatism, vol. 29, No. 8, Aug. 1986, pp. 1039-1049.
AminoActiv Webpage, copyright 2012, http://aminoactiv.com/faq/.
Patani, George et al., "Bioisosterism: A Rational Approach in Drug Design", Chem. Rev. 1996, 96, 3147-3176.
AminoActiv, FAQ, 1-3, Mar. 17, 2013 [retrieved on Feb. 19, 2015], Retrieved from the Internet, <URL: https://web.archive.org/web/20130317070349/http://aminoactiv.com/faq/>, entire document.
AminoActiv, Uses & Doses, 1-2, Mar. 17, 2013, [retrieved on Feb. 19, 2015], Retrieved from the Internet, <URL: https://web.archive.org/web/20130317014703/http://aminoactiv.com/health-professional/treatment-for-pain-conditions/>, entire document.
International Search Report dated Apr. 13, 2015 of corresponding International Patent Application No. PCT/US2014/070615.

* cited by examiner

*Primary Examiner* — Adam C Milligan
*Assistant Examiner* — William Y Lee
(74) *Attorney, Agent, or Firm* — Bradley Arant Boult Cummings LLP

(57) ABSTRACT

A method and composition for treating osteoarthritis including administering an anti-inflammatory agent to a patient, wherein the anti-inflammatory agent is ethyl (α-guanido-methyl) ethanoate. Ethyl (α-guanido-methyl) ethanoate provides a safe, non-toxic anti-inflammatory treatment for osteoarthritis.

10 Claims, 4 Drawing Sheets

METHOD AND COMPOSITION FOR TREATING OSTEOARTHRITIS

FIELD OF THE INVENTION

This invention relates to a method for treating osteoarthritis. In particular, the present invention is directed to a safe, non-toxic anti-inflammatory treatment for osteoarthritis. The present invention also relates to the anti-inflammatory agents for use in the method.

BACKGROUND OF THE INVENTION

Osteoarthritis ("OA") is a prevalent, painful, but treatable inflammatory disease that affects millions of Americans. While current treatment modalities include weight reduction and various dietary supplements, such as glucosamine, chondroitin, and green lip mussel, OA is most commonly treated with a class of drugs known as non-steroidal anti-inflammatory drugs ("NSAIDs"), e.g., ibuprofen and Rimadyl. NSAIDs are generally effective but have a number of toxic side effects that compromise the gastrointestinal, renal, and/or cardiovascular health of many patients.

It is clinically known that NSAID side effects include stomach bleeding, heart risks, and liver and kidney toxicity. These side effects have been directly linked to inhibition of the cyclooxygenase ("COX") enzyme, the anti-inflammatory mechanism of action for NSAIDs. Recently, there has also been research that shows current NSAID treatment increases oxidative stress which, in turn, initiates an overall degradation of a person's health and immune system and results in the slowed healing of bones, tendons, ligaments, and muscles. In addition, NSAIDs may become addictive.

The market has attempted to develop less toxic alternatives that are still effective at providing relief and pain management. However, attempts to date have been relatively unsuccessful. Compounds that were considered "safe" for use either did not prove to effectively reduce inflammation in cases like OA or expressed unexpected toxicity in certain situations or among certain groups of patients. Given the current therapeutic options available, there remains a need for additional treatments to effectively manage the pain and reduced mobility associated with OA without the toxic side effects provided by current over-the-counter and prescription NSAIDs.

SUMMARY OF THE INVENTION

The present invention is directed to a method for treating an inflammatory disease, such as osteoarthritis, including administering an anti-inflammatory agent to a patient, wherein the patient may be a human or an animal, and wherein the animal may be a canine, wherein the anti-inflammatory agent includes ethyl ($\alpha$-guanido-methyl) ethanoate. While the mechanism by which ethyl ($\alpha$-guanido-methyl) ethanoate acts at the cellular level is likely to involve multiple anti-inflammatory pathways, they are unique from NSAIDs and other dietary supplements in current use for treating OA. In one embodiment, the anti-inflammatory agent is administered to the patient in an oral dosage or as a topical application. The topical application may be administered in an amount of about 0.5 mL to about 5 mL. The oral dosage may be administered in an amount of about 400 mg to about 2400 mg.

The present invention is also directed to a method for reducing acute blood levels of pro-inflammatory marker, serum amyloid A, including administering an anti-inflammatory agent to a patient, wherein the anti-inflammatory agent is ethyl ($\alpha$-guanido-methyl) ethanoate. In one embodiment, the acute blood levels of serum amyloid A are reduced by about 30 percent to about 70 percent when compared to levels of serum amyloid A prior to administration of the anti-inflammatory agent. In this aspect of the invention, the anti-inflammatory agent may be administered to the patient in an oral dosage of about 400 mg to about 2400 mg.

In another aspect, the present invention is directed to a method for reducing production and release of pro-inflammatory prostanoids in cells including administering an anti-inflammatory agent to a patient, wherein the anti-inflammatory agent is ethyl ($\alpha$-guanido-methyl) ethanoate. In one embodiment, the pro-inflammatory prostanoids are reduced by about 50 percent or more when compared to an amount of pro-inflammatory prostanoids prior to administration of the anti-inflammatory agent. In another embodiment, the pro-inflammatory prostanoids are reduced by about 70 percent or more when compared to an amount of pro-inflammatory prostanoids prior to administration of the anti-inflammatory agent. In this aspect, the pro-inflammatory prostanoids include prostaglandin $E_2$.

In yet another aspect, the present invention is directed to a method for reducing levels of serum amyloid A, pro-inflammatory prostanoids, and tumor necrosis factor alpha in a patient, including administering an effective amount of ethyl ($\alpha$-guanido-methyl) ethanoate to the patient. In one embodiment, the levels of serum amyloid A are reduced by about 40 percent to about 60 percent when compared to levels of serum amyloid A prior to administration of the ethyl ($\alpha$-guanido-methyl) ethanoate; the levels of pro-inflammatory prostanoids are reduced by about 50 percent or more when compared to levels of pro-inflammatory prostanoids prior to administration of the ethyl ($\alpha$-guanido-methyl) ethanoate; and the levels of tumor necrosis factor alpha are reduced by about 40 percent to about 60 percent when compared to levels of tumor necrosis factor alpha prior to administration of the ethyl ($\alpha$-guanido-methyl) ethanoate. In this aspect, the effective amount of ethyl ($\alpha$-guanido-methyl) ethanoate is an oral dosage of about 400 mg to about 2400 mg. The ethyl ($\alpha$-guanido-methyl) ethanoate may also be administered with at least one other compound including homeopathic compounds, co-medications, nutraceuticals, plant extracts, herbal preparations, and cosmetic agents.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

Figure 1:
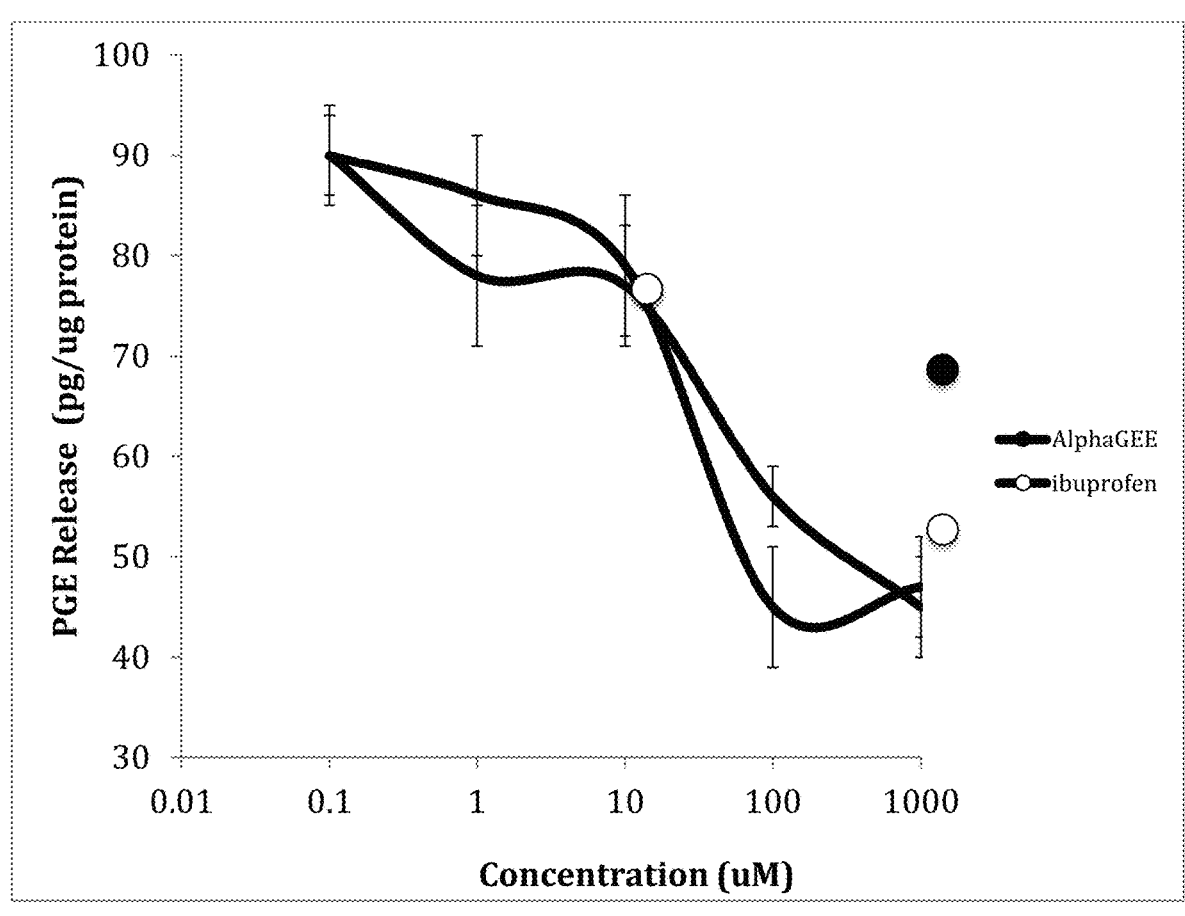
FIG. 1 is a graph comparing the effects of ibuprofen and Alpha-GEE on the release of prostaglandin $E_2$ ("PGE₂") in brain endothelial cells.

The present invention is directed to a method for treating OA, the anti-inflammatory agents and compositions useful in the method, and kits for application of the method. In particular, the present invention provides a method for safe, non-toxic relief from the pain and inflammation caused by OA. In one embodiment, the method of the present invention includes administering an anti-inflammatory agent to a patient in order to reduce pain and increase lost mobility associated with OA.

The Compound

Arthritis, such as OA, is an inflammatory condition within the joint that occurs through activation and interaction of multiple inflammatory cascades. Without being bound by any particular theory, the common pathways for inflammatory conditions are believed to include: 1) infiltration of immune macrophage cells into the joint and activation of toll receptors on immune cells and chondrocyte cells within the joint; 2) release of multiple proinflammatory cytokines from chondrocytes within the joint; 3) production and release of inflammatory arachidonic acid metabolites (prostaglandins); and 4) mitochondrial dysfunction. Current anti-inflammatory treatments, including conventional NSAIDs, are directed at preventing arachidonic acid metabolites (e.g., prostaglandins) from being produced and released. These treatments involve the suppression or inhibition of the cyclooxygenase enzymes. While such treatments can reduce the pain caused by osteoarthritis, it represents a rather late stage component of the inflammatory process. Thus, conventional NSAIDs treat the pain produced by inflammation within the arthritic joint, but have minimal impact on the inflammation present.

In contrast, the compound of the present invention is an anti-inflammatory agent that is unique in that it works in a pro-inflammatory manner. Unlike conventional NSAIDs, the compound of the present invention prevents prostaglandin production and release without direct inhibition of cyclooxygenase enzymes. In other words, rather than masking pain by blocking sensory perception/neuro-communicative pathways, the anti-inflammatory agent for use in the method of the present invention attacks the "origin" of inflammation, i.e., mitochondrial dysfunction. In particular, the anti-inflammatory agent of the present invention stabilizes the mitochondrial transition permeability, which is important to the ionic gradient and health of the mitochondria, and thus prevents leakage of various proteins that then induce a cytokine response which starts the chemical cascade that is consistent with the inflammatory model.

In one embodiment, the anti-inflammatory agent may include ethyl (α-guanido-methyl) ethanoate ("Alpha-GEE"). Data indicates that Alpha-GEE has a positive effect on toll receptors. Toll receptors act as a key part of our body's recognition mechanism and appear to be a major factor in the onset and/or progression of various medical indications including those that involve inflammation and pain. In particular, real time PCR or immunofluorescent staining of exposed cells was used to assess expression of toll-like receptor-2 (TLR-2), TLR-3, TLR-4, and TLR-7. Alpha-GEE appears to possess immunostimulatory properties and increases expression of TLR-2, TLR-3, TLR-4, and TLR-7 in cells. Without being bound by any particular theory, the mechanism by which TLR expression seems to be altered involves decreased pro-inflammatory mediator production in the wake of exposure to Alpha-GEE.

Alpha-GEE may be produced via acid-catalyzed conjugation of three amino acids. Once conjugated, the amino acids demonstrate anti-inflammatory properties comparable, if not superior, to conventional NSAIDs. For example, the anti-inflammatory agent, Alpha-GEE, has been found to reduce numerous inflammatory markers in the body including prostaglandin $E_2$ ("$PGE_2$") plasma levels, serum amyloid A ("SAA") levels, and tumor necrosis factor alpha ("TNFα") levels.

In one embodiment, the anti-inflammatory agent of the present invention has been found to reduce production and release of pro-inflammatory prostanoids in cells. Pro-inflammatory prostanoids are mediators in inflammatory reactions and include prostaglandin $E_2$ ("$PGE_2$"). The anti-inflammatory agent of the present invention has been found to reduce $PGE_2$ levels by about 50 percent or more with Alpha-GEE concentrations of about 20 µM or more. In one embodiment, the reduction of $PGE_2$ levels is about 55 percent or more at an Alpha-GEE concentration level of about 20 µM or more. In another embodiment, the effects of Alpha-GEE at a concentration of about 20 µM or more result in a reduction of $PGE_2$ release of about 60 percent or more. In yet another embodiment, the effects of Alpha-GEE at a concentration of about 20 µM or more result in a reduction of $PGE_2$ release of about 70 percent or more. For example, a concentration of about 20 µM or more of Alpha-GEE may result in a reduction of $PGE_2$ release in brain endothelial cells of at least 50 percent or more, preferably about 55 percent or more, more preferably about 60 percent or more, and even more preferably about 70 percent or more.

When the concentration of Alpha-GEE is about 100 µM or more, the reduction of $PGE_2$ levels is about 55 percent or more. In another embodiment, the effects of Alpha-GEE at a concentration of about 100 µM or more result in a reduction of $PGE_2$ release of about 60 percent or more. In yet another embodiment, the effects of Alpha-GEE at a concentration of about 100 µM or more result in a reduction of $PGE_2$ release of about 70 percent or more. For example, a concentration of about 100 µM or more of Alpha-GEE may result in a reduction of $PGE_2$ release in brain endothelial cells of at least 50 percent or more, preferably about 55 percent or more, more preferably about 60 percent or more, and even more preferably about 70 percent or more.

Administration of Alpha-GEE at concentrations of about 100 µM results in about 50 percent reduction in $PGE_2$ release after about four hours. In one embodiment, at least about a 60 percent reduction in $PGE_2$ release is observed after about a four hour treatment with Alpha-GEE. For example, a concentration of about 100 µM of Alpha-GEE may result in a reduction of $PGE_2$ release in canine chondrocytes of about 50 percent, preferably about 60 percent, after about a four hour treatment.

In another embodiment, at least about a 60 percent reduction in $PGE_2$ release is observed after about an eight hour treatment with Alpha-GEE. In yet another embodiment, at least about a 70 percent reduction in $PGE_2$ release is observed after about an eight hour treatment of the with Alpha-GEE. In still another embodiment, administration of Alpha-GEE results in at least about a 75 percent reduction in $PGE_2$ release after about eight hours. In particular, administration of Alpha-GEE may result in a reduction of $PGE_2$ release in canine chondrocytes of at least about 60 percent, preferably at least about 70 percent, and more preferably at least about 75 percent, after about an eight hour treatment In this aspect of the invention, comparing the reduction of $PGE_2$ release over a four to eight hour time period when treated with Alpha-GEE, NSAID (Rimadyl), glucosamine, or a TNFα receptor, Alpha-GEE has the most rapid effect on the reduction of $PGE_2$ release. Accordingly, in one embodiment, Alpha-GEE has at least about a 10 percent greater reduction in $PGE_2$ release after about four hours as compared to NSAID (Rimadyl), glucosamine, and a TNFα receptor blocker (inhibitor). In another embodiment, Alpha- GEE has at least about a 20 percent greater reduction in $PGE_2$ release after about four hours as compared to NSAID (Rimadyl), glucosamine, and a $TNF\alpha$ receptor blocker. In another embodiment, Alpha-GEE has at least about a 25 percent greater reduction in $PGE_2$ release after about four hours as compared to NSAID (Rimadyl), glucosamine, and a $TNF\alpha$ receptor blocker. For example, Alpha-GEE has at least about a 10 percent greater, preferably about 20 percent greater, more preferably about 25 percent greater, reduction in $PGE_2$ release in canine chondrocytes after about four hours as compared to NSAID (Rimadyl), glucosamine, and a $TNF\alpha$ receptor blocker (inhibitor).

The release of $PGE_2$ is reduced by at least about 10 percent from the fourth hour post-administration with Alpha-GEE to the eighth-hour post-treatment with Alpha-GEE. In one embodiment, $PGE_2$ release is reduced by at least about 15 percent from hour 4 to hour 8 when Alpha-GEE is administered. For example, $PGE_2$ release in canine chondrocytes is reduced by at least about 10 percent, preferably at least about 15 percent, from hour 4 to hour 8 when Alpha-GEE is administered.

While the reduction in prostaglandin release observed with Alpha-GEE are somewhat similar in magnitude to that observed with NSAID treatment, the anti-inflammatory pathway for Alpha-GEE is believed to be different from that of NSAIDs commonly used to treat conditions such as OA. As such, in one embodiment, administration of Alpha-GEE over a concentration range of 0.1 to 100 μM shows little to no change in percent inhibition of cyclooxygenase ("COX") activity. In one embodiment, administration of Alpha-GEE in an amount of 0.1 μM results in about 20 percent inhibition of cyclooxygenase-1 ("COX-1") activity, while administration of Alpha-GEE in amounts of 1 μM and 100 μM results in about 20 percent inhibition, about 15 percent inhibition, and about 15 percent inhibition of COX-1 activity, respectively. In another embodiment, administration of Alpha-GEE in an amount of 0.1 μM results in about 10 percent inhibition of cyclooxygenase-2 ("COX-2") activity, while administration of Alpha-GEE in amounts of 1 μM and 100 μM results in about 15 percent inhibition, about 18 percent inhibition, and about 15 percent inhibition of COX-2 activity, respectively. Accordingly, as Alpha-GEE does not demonstrate a concentration dependency, there is no mechanistic inhibition of the COX enzymes.

In one embodiment, administration of Alpha-GEE at any concentration ranging from 0.1 μM to 100 μM results in less than about a 10 percent deviation in inhibition of the activity of COX-1, COX-2, or both. In another embodiment, administration of Alpha-GEE at any concentration ranging from 0.1 μM to 100 μM results in about a 5 percent or less deviation in inhibition of the activity of COX-1. In yet another embodiment, administration of Alpha-GEE at any concentration ranging from 0.1 μM to 100 μM results in about an 8 percent or less deviation in inhibition of the activity of COX-2.

In this aspect of the invention, the administration of Alpha-GEE results in less than about 10 percent inhibition of the activity of cyclooxygenase-1 ("COX-1"), cyclooxygenase-2 ("COX-2"), or both. In one embodiment, the activity of COX-1, COX-2, or both is inhibited by less than about 7 percent upon administration of Alpha-GEE. In another embodiment, the administration of Alpha-GEE results in less than about 5 percent inhibition of the activity of COX-1, COX-2, or both. In yet another embodiment, the administration of Alpha-GEE results in less than about 3 percent inhibition of the activity of COX-1, COX-2, or both. In still another embodiment, the administration of Alpha- GEE results in less than about 1 percent inhibition of the activity of COX-1, COX-2, or both.

In another embodiment, the anti-inflammatory agent of the present invention has been found to reduce acute blood levels of the pro-inflammatory marker, SAA. SAA proteins are expressed in response to inflammatory stimuli. Administration of the anti-inflammatory agent of the present invention results in the reduction of acute blood levels of SAA by at least about 30 percent to about 70 percent compared to values prior to treatment. In one embodiment, when Alpha-GEE is administered, the SAA levels are reduced by about 40 percent to about 60 percent compared to values prior to treatment. In particular, one embodiment contemplates a reduction of acute blood levels of SAA by about 30 percent to about 70 percent when canines receive a dose of at least about 36 mg/kg over a two-week period.

In yet another embodiment of the present invention, the anti-inflammatory agent has been found to reduce the release of $TNF\alpha$. $TNF\alpha$ is a cytokine involved in systemic inflammation. $TNF\alpha$ produces much of the inflammation that leads to cartilage destruction in the joint, as well as contributing to $PGE_2$ production through COX-2 enzyme induction. The anti-inflammatory agent of the present invention has been found to reduce $TNF\alpha$ release by about 40 percent to about 60 percent after a time period of about 8 to about 48 hours post-treatment. In one embodiment, the reduction in $TNF\alpha$ release is about 45 percent to about 55 percent after a time period of about 8 to about 48 hours post-treatment. For example, administration of Alpha-GEE has been found to reduce $TNF\alpha$ release in canine chondrocytes by about 40 percent to about 60 percent, preferably by about 45 percent to about 55 percent, after a time period of about 8 to about 48 hours post-treatment.

In particular, the anti-inflammatory agent of the present invention has been found to reduce $TNF\alpha$ release by at least about 20 percent after a time period of about 8 to about 24 hours post-treatment. In one embodiment, the anti-inflammatory agent of the present invention has been found to reduce $TNF\alpha$ release by at least about 30 percent after a time period of about 8 to about 24 hours post-treatment. In another embodiment, the anti-inflammatory agent of the present invention has been found to reduce $TNF\alpha$ release by at least about 40 percent after a time period of about 8 to about 24 hours post-treatment. For example, administration of Alpha-GEE has been found to reduce $TNF\alpha$ release in canine chondrocytes by at least about 20 percent, preferably at least about 30 percent, and more preferably at least about 40 percent, after a time period of about 8 to about 24 hours post-treatment.

In still another embodiment, the reduction in $TNF\alpha$ release is at least about 50 percent after a time period of about 48 hours post-treatment. In yet another embodiment, the reduction in $TNF\alpha$ release is at least about 60 percent after a time period of about 48 hours post-treatment. For example, administration of Alpha-GEE has been found to reduce $TNF\alpha$ release in canine chondrocytes by at least about 50 percent, preferably at least about 60 percent, after a time period of about 48 hours post-treatment.

Administration

The anti-inflammatory agent may be produced in powder or crystal form. In one embodiment, the anti-inflammatory agent is encapsulated or tableted for an oral dosage. For example, the anti-inflammatory agent may be administered in the form of a pill, tablet, capsule, or gel capsule. In another embodiment, the anti-inflammatory agent may be administered in a liquid form. For example, the anti-inflammatory agent may be administered as an elixir. In yet another embodiment, the anti-inflammatory agent may be blended into a cream for a topical application. The anti-inflammatory agent may also be encompassed in a gel or similar form for topical application.

In one embodiment, the anti-inflammatory agent is administered orally to a patient. A patient may include, but is not limited to, a human, a canine, and an animal. Oral dosages range from use "as needed" to daily dosages of 1-2 capsules taken 1-3 times daily depending on the severity of symptoms. In one embodiment, an effective oral dosage of the anti-inflammatory agent ranges from about 400 mg to 2400 mg per day, or about 5 mg/kg to about 30 mg/kg. In another embodiment, an effective oral dosage ranges from about 400 mg to about 800 mg, or about 5 mg/kg to about 10 mg/kg. In yet another embodiment, an effective oral dosage ranges from about 400 mg to about 1200 mg, or about 5 mg/kg to about 15 mg/kg.

The anti-inflammatory agent may also be administered to the site as a topical cream or gel. In one embodiment, an effective topical cream or gel dosage ranges from use "as needed" to 1 mL-10 mL applied 1-4 times daily while cleansing the area between uses to keep pores open. In another embodiment, an effective topical cream or gel dosage ranges from about 0.5 mL to about 5 mL applied 1-4 times daily.

The anti-inflammatory agent of the present invention may be blended with or administered in conjunction with at least one other compound. In one embodiment, the at least one other compound includes a homeopathic compound, a co-medication, a nutraceutical, a plant extract, a herbal preparation, a cosmetic agent, a pharmaceutical, or combinations thereof. In another embodiment, the anti-inflammatory agent is present in a composition or blend with at least two other compounds.

Suitable homeopathic compounds include, but are not limited to, *Actaea spicata, Aesculus hippocastanum, Arnica montana, belladonna, Bellis perennis, bryonia, calcarea carbonica, Calcarea fluorica,* calc sulph MM, causticum, cayenne, *Cimicifuga racemosa, Formicum acidum, Hamamelis virginiana, Hypericum perforatum, Magnesia phosphorica, Phytolacca decandra, pulsatilla, Rhododendron* chrysanthum, *Rhus toxicodendron, Ruta graveolens, Salicylicum acidum, sepia, sulphu,* turmeric, green tea extract, grape extract, *foeniculum vulgare, Bellis perrinis, Boswellia serrate, bromeliaceae,* devil's claw (*Harpagophytum procumbens*), *bromelain, Cordyalis yanhusuo,* or combinations thereof.

Although the present invention has been described in terms of treating a patient having osteoarthritis, the present invention contemplates the use of the anti-inflammatory agent of the present invention to treat other inflammatory joint diseases. For example, the anti-inflammatory agent of the present invention may be used to treat different types of arthritis including rheumatoid arthritis.

EXAMPLES

The following non-limiting examples are merely illustrative of the preferred embodiments of the present invention, and are not to be construed as limiting the invention, the scope of which is defined by the appended claims.

Example 1: Double Blind Randomized Trial in OA Canines

The following example evaluates the effectiveness of Alpha-GEE on both pain and mobility in a double-blind randomized trial in canines having OA. Results of the study indicate that evaluation of pain and mobility during the course of the trial demonstrated a significant improvement in canines receiving Alpha-GEE compared to canines in the placebo group with score reductions of approximately 50 percent versus 15 percent, respectively. Furthermore, while pedometer measurements showed no significant changes in the mobility of canines in the placebo group, the canines treated with Alpha-GEE showed an approximately 30 percent increase in physical activity during the two-week trial period. No significant differences were observed in prostaglandin $E_2$ ("$PGE_2$") plasma levels during the trial period in either treatment group; however serum amyloid A ("SAA") levels were lower in canines in the Alpha-GEE treatment group compared to placebo at the end of the study. Together these findings provide clinical evidence of the effectiveness of treatments with Alpha-GEE in reducing the pain and restricted mobility of canines with OA.

Study Design

The double-blind study was performed on a total of 30 adult canines of various breeds in five different private practice clinics. Owner consent was obtained prior to participation in the study. Each clinic was responsible for enrolling 6 canines into the study. Inclusion criteria for the study consisted of clinical assessment and radiograph confirmation of OA in at least one joint and a score of 22 or greater on the Helsinki chronic pain index ("HCPI"). Use of NSAIDs or other dietary supplements for OA were allowed, provided the current treatment regimens had not been altered for a period of at least three months. A randomized block design was used with canines assigned in a one to one ratio into either placebo (36 mg/kg/day maltose-dextran; Vireo Resources, Plattsmouth, NE) or Alpha-GEE (36 mg/kg/day; Vireo Resources, Plattsmouth, NE) treatment group. The block size was six canines, corresponding to the total number of canines enrolled from each clinic. Group assignments for each canine were blinded to both the owners and attending veterinarian until all the data was collected and reported. Both Alpha-GEE and placebo were provided in 400 mg capsules and owners were instructed on the proper method for daily oral administration of capsules to their canines and provided with the appropriate number of capsules for the duration of the 2-week study. Blood samples were taken at both the start and conclusion of the two-week trial period to monitor for changes in blood chemistry as well as potential changes in inflammatory markers as described below. Owners completed the HCPI prior to starting the study, one-week after starting the study, and a final time at the conclusion of the study at two-weeks.

Canines participating in the study were also fitted with pedometers (Draco Tech International, Taiwan) to quantitatively track changes in daily activity during the course of the study. Use of pedometers to quantitatively assess activity has been demonstrated previously. The pedometers were fitted onto the collars at the clinic, and owners were instructed on care and maintenance of the pedometers and provided a log book to record the daily pedometer readings. Pedometer readings were recorded on a daily basis starting one week prior to the study and continuing throughout the two-week trial period. The daily pedometer readings recorded throughout an entire week (7-day period) were used to determine the average daily activity during the baseline period (one week prior to the start of the study) and the first and second weeks of the trial. Averaging of the daily pedometer readings over a 7-day period has been shown previously to provide the best reductions in intra and inter subject variability. Treatment-dependent changes in the activity of the canines were assessed by examining the changes in average daily pedometer readings from the first and second week periods to the average daily pedometer readings from the baseline period obtained prior to the start of the study.

Measurement of Inflammatory Markers in Plasma

In addition to the standard blood chemistry profile, blood samples taken before and at the conclusion of the two-week trial period were analyzed for $PGE_2$ and SAA. Blood samples were collected in heparin tubes for $PGE_2$ and in serum collection tubes for SAA. Both plasma and serum samples were centrifuged at 2000×g for 10 minutes and the plasma and serum supernatants removed and frozen at 20° C. until analyzed for $PGE_2$ and SAA using enzyme-linked immunosorbent assays ("HA"). Of the 30 canines enrolled, 8 were excluded from the blood analysis portion of the study due to sampling/storage issues resulting in a lack of a pre- or post-trial sample. As $PGE_2$ is rapidly metabolized in plasma, measurement of $PGE_2$ metabolites is the most reliable method for assessing plasma levels of $PGE_2$. Plasma samples were analyzed for $PGE_2$ using the bicycle $PGE_2$ competitive EIA kit purchased from Cayman Chemical (Ann Arbor, MI). The assay converts $PGE_2$ metabolites into a stable derivative that is measured using EIA. Samples (100 μl) were analyzed in triplicate and $PGE_2$ concentrations determined by use of standard curve. For SAA measurements, a solid phase sandwich EIA kit (Tridelta Development Ltd, Maytooth, Co Kildare, Ireland) was used as described previously.

Statistics

Statistical evaluations of pain (HCPI), mobility (pedometer readings), and inflammatory markers were performed using ANOVA and Student Newman Keuls post-hoc comparison of means.

Results

A total of 30 canines of various breeds were enrolled in the study. A total of 28 canines completed the study with one canine in the placebo group discontinuing due to gastrointestinal irritation and one canine in the Alpha-GEE group removed due to a brain tumor discovered after partial completion of the trial. As shown in Table 1 below, information concerning the general demographics of the two groups is summarized. The age and sex of the canines were comparable in both treatment groups. A total of 4 canines in the placebo group were maintained on NSAIDs and/or dietary supplements for OA, compared to 3 canines in the Alpha-GEE treatment group. The average number of joints with radiograph confirmation of OA in the placebo and Alpha-GEE group was 2 and 3, respectively.

TABLE 1

| Characteristics of OA Canines Enrolled In Trial | | | | | | | |
|---|---|---|---|---|---|---|---|
| | Age (yrs) | | | | Weight (lbs) | | Current Meds | Joints with OA |
| | Mean ± SD | Range | # of Males | # of Females | Mean ± SD | range | # canines | Mean ± SD |
| Placebo | 12 ± 3 | 7-15 | 8 | 7 | 58 ± 21 | 17-90 | 4/14 | 2 ± 1 |
| Alpha-GEE | 11 ± 3 | 5-14 | 7 | 8 | 60 ± 29 | 13-100 | 3/14 | 3 ± 1 |

Owner assessment of pain and mobility in canines participating in the trial were based on the HCPI. The HCPI is a method for appraisal of pain and mobility in canines. The assessment is based on owner responses to eleven questions with a numerical answer between 0-4. Scoring on the HCPI ranges from 0 to 44, with higher numbers reflecting more pain and immobility present in the canine. Canines in both placebo and treatment group had similar initial pre-trial HCPI scores. After the first week of the trial, modest improvements in the HCPI score were observed in both the placebo and Alpha-GEE treatment groups. However, the reductions (approximately 10-15 percent in magnitude) in HCPI scores obtained in both the placebo and Alpha-GEE treatment groups after the first week resulted in HCPI scores that were not statistically different from each other. While no further improvements were observed after the second week of the trial in the canines receiving placebo, the HCPI scores were further reduced in the Alpha-GEE treatment group from the pre-trial values of 28 to post-trial values of 15. This represents an approximately 46 percent reduction from the original pre-trial values. The HCPI scores at the conclusion of the study in the Alpha-GEE treatment group were significantly different ($p<0.001$) from that of the placebo group. The magnitude of change in HCPI scores during the entire trial ranged from $-1$ to 9 (with mean+SD=3+4) for placebo compared to 2 to 20 (with mean+SD=13+7) for Alpha-GEE treated canines.

The activity levels of the canines in the study were also assessed during the two-week trial. Pedometer readings from the canines in the placebo group did not change significantly over the trial period. In contrast, canines in the Alpha-GEE treatment group displayed significant increases in daily pedometer readings (i.e., mobility) at both the first (approximately 20 percent increase) and second (approximately 30% increase) week of the trial. The recorded changes in weekly pedometer readings in the Alpha-GEE treatment group were significantly different from that of the placebo group after both the first ($p<0.05$) and second ($p<0.01$) weeks of the trial.

The standard blood chemistry profiles of the canines enrolled in the study are shown in Table 2.

TABLE 2

| Blood Chemistry Profile of OA Canines For Trial Period | | | | | | |
| --- | --- | --- | --- | --- | --- | --- |
| | | Placebo | | Alpha-GEE | | |
| Parameter | | Pre-Trial | Post-Trial | Pre-Trial | Post-Trial | Normal Range |
| ALT (U/L) | Mean ± SD | 63 ± 55 | 60 ± 52 | 89 ± 99 | 53 ± 37 | 10-118 U/L |
| | range | 18-235 | 10-160 | 10-403 | 10-95 | |
| ALP (U/L) | Mean ± SD | 207 ± 167 | 243 ± 194 | 110 ± 104 | 103 ± 131 | 20-150 U/L |
| | range | 31-584 | 53-654 | 24-368 | 25-382 | |
| Glucose (mg/dL) | Mean ± SD | 101 ± 15 | 102 ± 19 | 102 ± 11 | 101 ± 11 | 80-110 mg/dL |
| | range | 91-114 | 91-115 | 75-125 | 87-116 | |
| Creatinine (mg/dL) | Mean ± SD | 1.1 ± 0.4 | 1.1 ± 0.4 | 1.2 ± 0.7 | 1.5 ± 0.7 | 0.3-1.4 mg/dL |
| | range | 0.7-1.7 | 0.8-1.4 | 0.7-2.5 | 0.8-2.5 | |
| BUN (mg/dL) | Mean ± SD | 18 ± 4 | 17 ± 4 | 24 ± 22 | 24 ± 19 | 7-25 mg/dL |
| | range | 12-29 | 8-27 | 8-66 | 8-65 | |
| Total Protein (g/dL) | Mean ± SD | 6.5 ± 0.7 | 6.7 ± 0.7 | 6.6 ± 0.4 | 6.5 ± 0.4 | 5.4-8.2 g/dL |

Not surprisingly, given the age of the canines in the study, there were values out of the normal range observed in both placebo and Alpha-GEE treatment groups. Aside from total protein in which there were no canines above the normal expected range, there was at least one canine in each treatment group that had values in the blood chemistry profile that were above the normal range. However, it should be noted that compared to the pre-trial values, there were no significant changes in the post-trial blood chemistry profiles during the trial period observed for either placebo or Alpha-GEE treated canines. Thus indicating that during the course of the two-week trial there were no significant changes in the blood chemistry profiles for canines in either placebo or Alpha-GEE treatment group.

Examination of $PGE_2$ and SAA, two inflammatory markers, was performed both prior to (pre-trial) and immediately following (post-trial) the two-week treatment period. As shown in Table 3, there was no difference in the pre-trial and post-trial plasma levels for $PGE_2$ in either the placebo or Alpha-GEE treated canines.

TABLE 3

Plasma Concentrations of Inflammatory Markers in OA Canines for the Trial Period

| Inflammatory Marker | | Pre-Trial Values | | Post-Trial Values | | |
| --- | --- | --- | --- | --- | --- | --- |
| | | Placebo | Alpha-GEE | Placebo | Alpha-GEE | P Value |
| $PGE_2$ | Mean ± SD | 250 ± 16 | 268 ± 11 | 275 ± 20 | 264 ± 10 | |
| (pg/ml) | 95% CI | 240-260 | 261-275 | 245-269 | 258-270 | |
| Serum Amyloid | Mean ± SD | 760 ± 752 | 673 ± 869 | 1483 ± 1653 | 255 ± 221* | 0.048 |
| A (ng/ml) | 95% CI | 368-1297 | 193-1297 | 555-2651 | 141-412 | |

*$p < 0.05$ compared to placebo at same time point

A wide range of values was obtained for SAA in both placebo and Alpha-GEE treatment groups. While there were no significant differences in the pre-trial levels of SAA in the placebo and Alpha-GEE groups, SAA levels were significantly lower in the Alpha-GEE treatment group at the conclusion of the study. Specifically, SAA levels were reduced by at least 30% and by as much as 70% from values prior to treatment with Alpha-GEE.

Example 2: Effects of Alpha-GEE and Ibuprofen on the Release of $PGE_2$ in Brain Endothelial Cells In this example, the effects of Alpha-GEE and Ibuprofen on the release of $PGE_2$ from brain endothelial cells were compared. The brain endothelial cells were first exposed to bacterial endotoxin. The effects of Alpha-GEE and Ibuprofen were then measured and the levels of release of $PGE_2$ were compared.

FIG. 1 demonstrates that the reduction in the release of $PGE_2$ from brain endothelial cells at an Alpha-GEE concentration of about 20 µM or more is about 50 percent or more. The reduction in the release of $PGE_2$ from brain endothelial cells at an Alpha-GEE concentration of about 1000 µM or more is greater than about 50 percent. The reduction of $PGE_2$ release observed with Alpha-GEE is similar in magnitude to the reduction of $PGE_2$ release observed with ibuprofen treatment.

Figure 2:
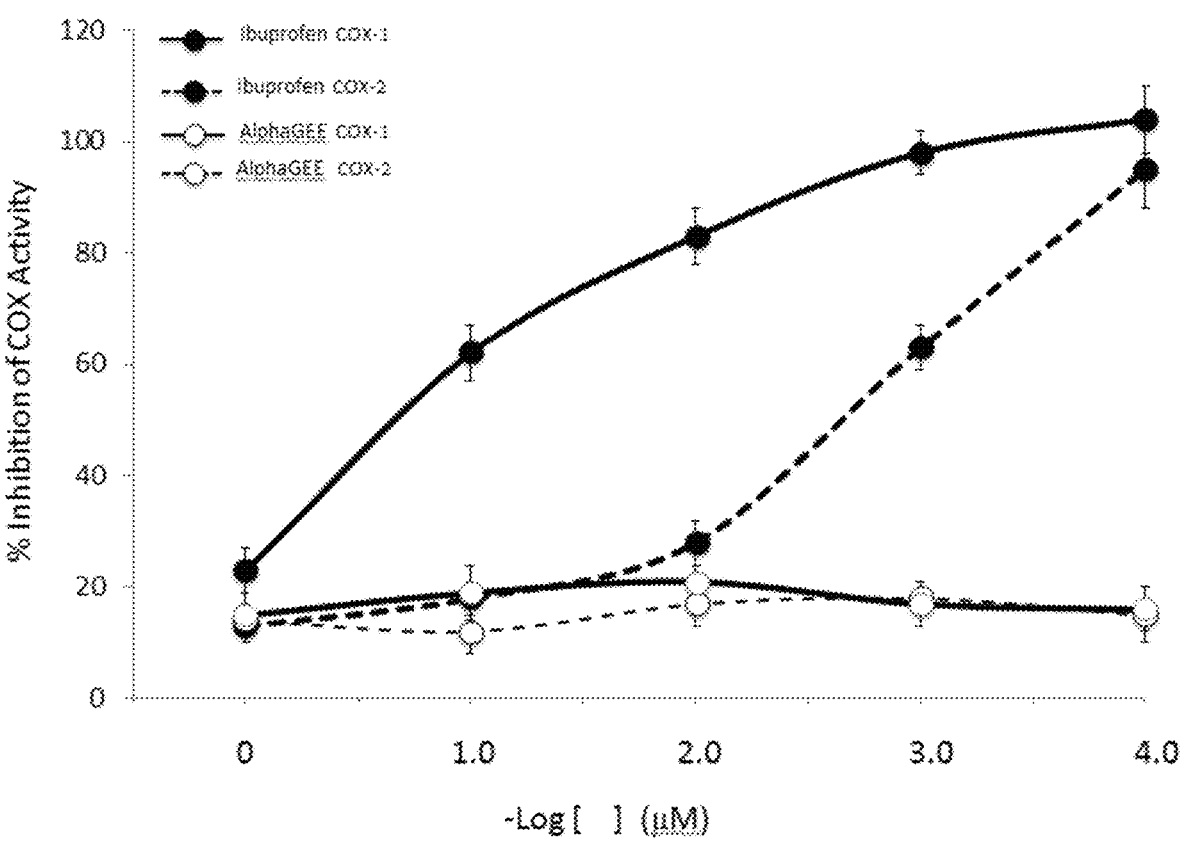
FIG. 2 is a graph comparing the effects of ibuprofen and Alpha-GEE on the inhibition of cyclooxygenase ("COX") activity.

Example 3: Effects of Alpha-GEE and Ibuprofen on Inhibition of Cyclooxygenase ("COX") Activity The effects of Alpha-GEE and Ibuprofen on the inhibition of cyclooxygenase-1 ("COX1") and cyclooxygenase-2 ("COX2") activity were also compared. As shown in FIG. 2, NSAIDs, such as ibuprofen, chemically bind to cyclooxygenase and inhibit prostaglandin production. Specifically, the NSAID, Ibuprofen, produced a concentration dependent inhibition of the COX enzymes when used at concentrations of 0.1-100 µM. For example, greater than about 60 percent of COX-1 and COX-2 activity is inhibited with Ibuprofen. In contrast, Alpha-GEE did not show a concentration dependency on the inhibition of COX enzymes. In other words, Alpha-GEE did not show a mechanistic inhibition of the COX enzymes. This suggests that the anti-inflammatory pathway for Alpha-GEE is different from that of NSAIDs commonly used to treat conditions such as OA.

Example 4: Effects of Alpha-GEE and Other Anti-Inflammatory Compounds on TNFα and PGE2 Release in Canine Chondrocytes The following example compares the effects of Alpha-GEE and other anti-inflammatory compounds on $PGE_2$ release, as well as TNFα release, in cultured canine chondrocytes.

The study involved the use of cultured canine chondrocytes (i.e., cells within the joint that are activated during OA). The canine chondrocytes were subjected to an inflammatory challenge in the form of cytokine Interleukin 1 beta ("IL1b"). The canine chondrocytes were then treated with various anti-inflammatory compounds including Alpha-GEE; glucosamine; a TNFα receptor antagonist; and a NSAID (Rimadyl). Alpha-GEE was administered in concentrations ranging from 10 µM to 1000 µM. The resulting effects of the various treatments on both $PGE_2$ release and TNFα release were examined.

Figure 3:
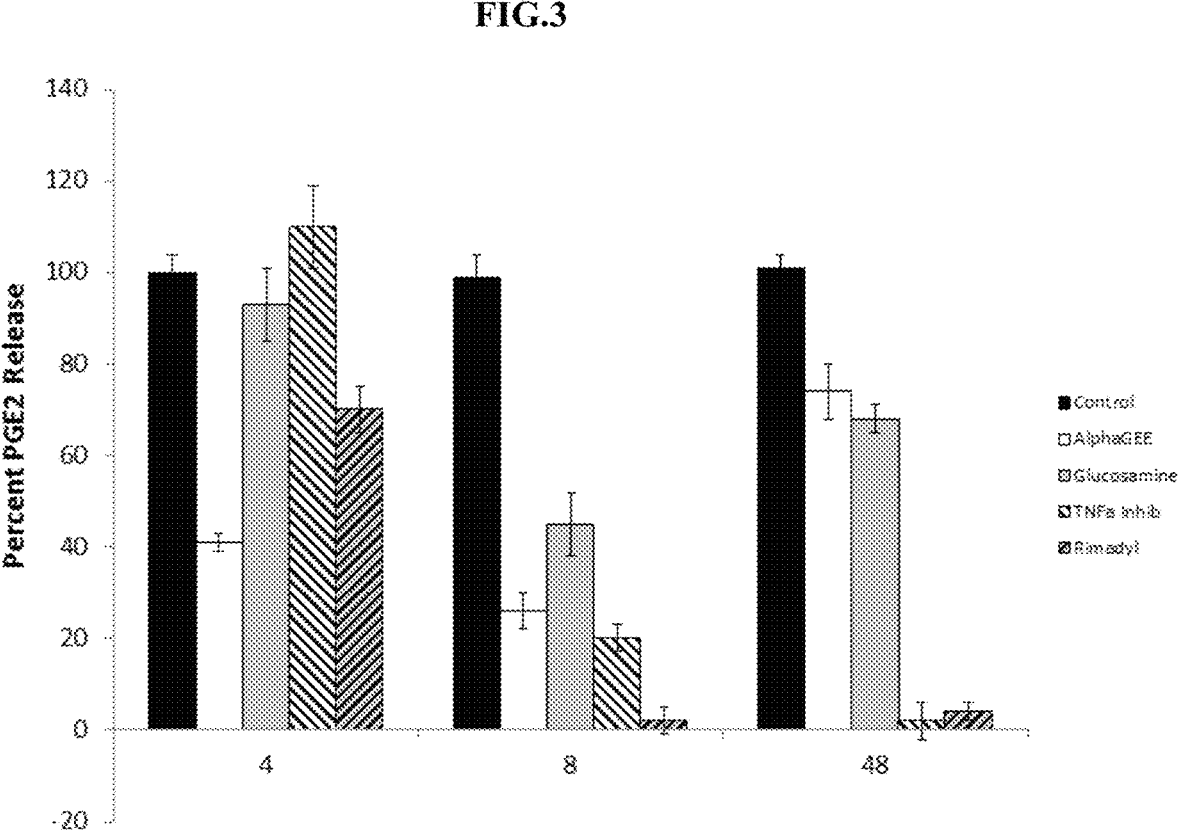
FIG. 3 is a graph comparing the effects of Alpha-GEE and other compounds on PGE₂ release in cultured canine chondrocytes.

As shown in FIG. 3, the results from the study showed a time-dependent reduction in $PGE_2$ release from chondrocytes following treatment with Alpha-GEE. Alpha-GEE, glucosamine, and Rimadyl were used in a concentration of 100 μM, while the TNFα inhibitor was used in a concentration of 1 μM. Based on all of the treatments examined (i.e., Alpha-GEE; glucosamine; NSAID (Rimadyl); and TNFα receptor antagonist), Alpha-GEE produced the most dramatic decrease in $PGE_2$ at the early 4-hour time point. The Alpha-GEE treatment showed an approximately 60 percent reduction in $PGE_2$ at 4 hours. The reduction in $PGE_2$ release at the early 4 hour time point was greater than that observed with the NSAID, Rimadyl, glucosamine, or TNFα receptor blocker. The maximal effect of Alpha-GEE on $PGE_2$ release from chondrocytes was observed within 8 hours, where a 75% reduction in $PGE_2$ release was observed. Maximal effects were observed at concentrations of Alpha-GEE of 100 μM. The effects of Alpha-GEE on $PGE_2$ release were consistently greater in magnitude than glucosamine and depending on the time examined, comparable to the NSAID or TNFα receptor antagonist.

Accordingly, the data in FIGS. 1, 2, and 3 collectively demonstrate that upon administration of Alpha-GEE, prostaglandin production and release is reduced without direct inhibition of cyclooxygenase enzymes, which is the mechanism of action of NSAIDs, such as ibuprofen and Rimadyl.

Figure 4:
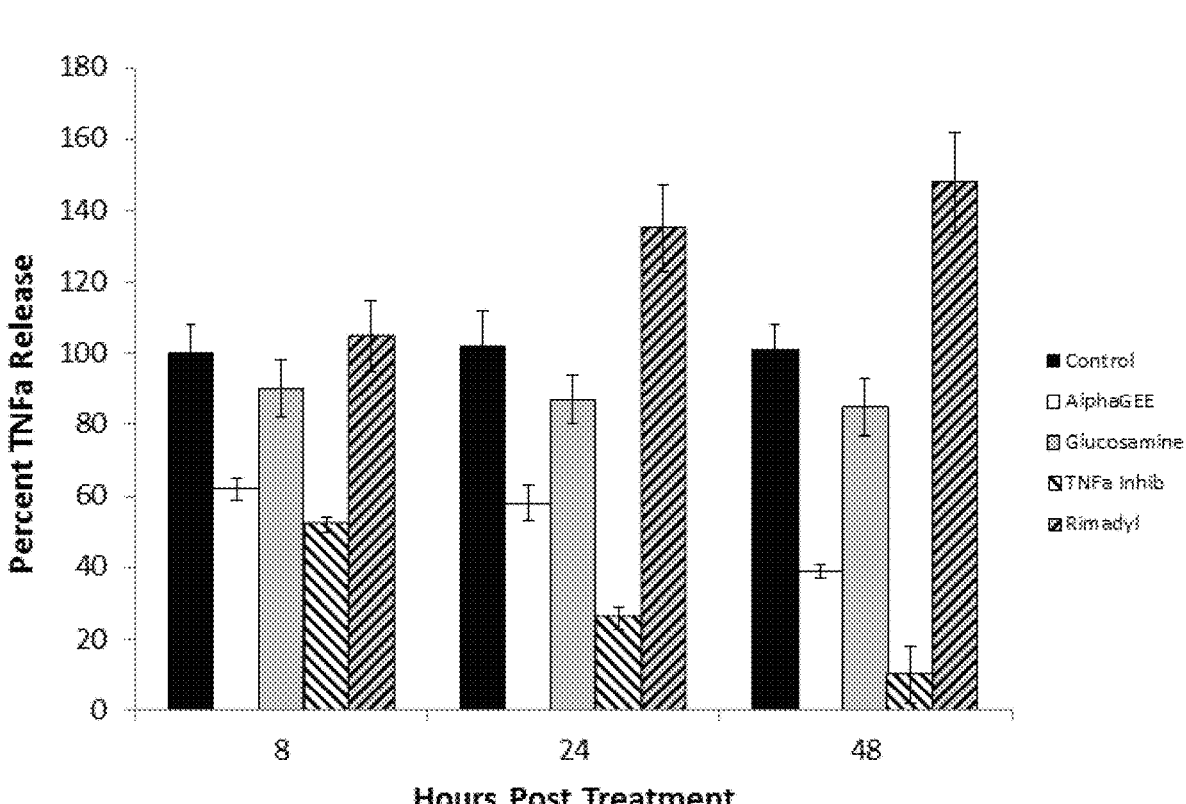
FIG. 4 is a graph comparing the effects of Alpha-GEE and other compounds on tumor necrosis factor alpha ("TNFα") release in cultured canine chondrocytes.

A similar time dependent decrease in TNFα release was also observed in chondrocytes treated with Alpha-GEE, as shown in FIG. 4. Alpha-GEE showed significant and sustained reductions in TNFα release from chondrocytes. The Alpha-GEE treatment demonstrated about 40 percent to about 60 percent reductions in TNFα release depending on the time point examined. This is in contrast to glucosamine that had no significant effect on TNFα release and Rimadyl, which produced a significant increase in TNFα release in chondrocytes.

Although the present invention has been described with reference to particular embodiments, it will be understood to those skilled in the art that the invention is capable of a variety of alternative embodiments within the spirit of the appended claims. For example, the method of the present invention is also contemplated for use as a preventative treatment to attenuate the effects of pain and inflammation associated with osteoarthritis.

What is claimed is:

1. A method of reducing release of TNF-α in canine chondrocytes comprising:

subjecting the canine chondrocytes to an inflammatory stimuli;

measuring a first level of TNF-α in the subjected canine chondrocytes;

treating the canine chondrocytes with a formulation for a first period of time, wherein the formulation comprises ethyl (α-guanido-methyl) ethanoate at a concentration of 10 μM to about 1000 μm, and wherein the first period of time is about 8 to about 48 hours;

measuring a second level of the TNF-α in the treated canine chondrocytes, wherein the second level is at least 20 percent less than the first level.

2. The method of claim 1, wherein the second level is at least 40 percent less than the first level.

3. The method of claim 1, wherein the first period of time is about 8 to about 24 hours.

4. The method of claim 1, wherein the second level is about 40 percent to about 60 percent less than the first level.

5. The method of claim 4, wherein the second level is about 45 percent to about 55 percent less than the first level.

6. A method of reducing release of TNF-α in canine chondrocytes subject to an inflammatory stimuli comprising:

measuring a first level of TNF-α in the canine chondrocytes;

treating the canine chondrocytes with a formulation for a first period of time, wherein the formulation comprises ethyl (α-guanido-methyl) ethanoate at a concentration of 10 μM to about 1000 μm, and where the first period of time is about 8 hours to about 24 hours;

measuring a second level of the TNF-α in the treated canine chondrocytes, wherein the second level is at least 20 percent less than the first level.

7. The method of claim 6, wherein the second level is at least 30 percent less than the first level.

8. The method of claim 6, wherein the inflammatory stimuli is cytokine Interleukin 1 beta.

9. A method of reducing release of TNF-α in canine chondrocytes subjected to an inflammatory stimuli comprising:

measuring a first level of TNF-α in canine chondrocytes;

treating the canine chondrocytes with a formulation for a first period of time, wherein the formulation comprises ethyl (α-guanido-methyl) ethanoate at a concentration of 10 μM to about 1000 μm, and where the first period of time is about 8 hours to about 48 hours;

measuring a second level of the TNF-α in the treated canine chondrocytes, wherein the second level is about 40 percent to about 60 percent less than the first level.

10. The method of claim 9, wherein the second level is about 45 percent to about 55 percent less than the first level.

* * * * *